US010386282B2

(12) United States Patent
Colomer Farrarons et al.

(10) Patent No.: US 10,386,282 B2
(45) Date of Patent: Aug. 20, 2019

(54) METHOD, APPARATUS AND MICRO-RHEOMETER FOR MEASURING RHEOLOGICAL PROPERTIES OF NEWTONIAN AND NON-NEWTONIAN FLUIDS

(71) Applicants: CONSORCI CENTRE DE RECERCA MATEMATICA, Bellaterra (ES); Jordi Colomer Farrarons, Sant Cugat del Valles (ES); Aurora Hernandez Machado, Barcelona (ES)

(72) Inventors: Jordi Colomer Farrarons, Sant Cugat del Valles (ES); Aurora Hernandez Machado, Barcelona (ES); Tomas Alarcon Cor, Barcelona (ES); Angeles Ivon Rodriguez Villarreal, Sant Cugat del Valles (ES); Pedro Luis Miribel Catala, Sant Pol de Mar (ES)

(73) Assignees: CONSORCI CENTRE DE RECERCA MATEMATICA, Bellaterra (ES); Jordi Colomer Farrarons, Saint Cugat del Valles (ES); Aurora Hernandez Machado, Barcelona (ES)

( * ) Notice: Subject to any disclaimer, the term of this patent is extended or adjusted under 35 U.S.C. 154(b) by 155 days.

(21) Appl. No.: 15/574,021

(22) PCT Filed: May 13, 2016

(86) PCT No.: PCT/EP2016/060835
§ 371 (c)(1),
(2) Date: Nov. 14, 2017

(87) PCT Pub. No.: WO2016/180964
PCT Pub. Date: Nov. 17, 2016

(65) Prior Publication Data
US 2018/0299361 A1 Oct. 18, 2018

(30) Foreign Application Priority Data

May 14, 2015 (EP) .................................. 15382248

(51) Int. Cl.
G01N 11/04 (2006.01)
G01F 1/64 (2006.01)
B01L 3/00 (2006.01)

(52) U.S. Cl.
CPC ............... *G01N 11/04* (2013.01); *G01F 1/64* (2013.01); *B01L 3/5027* (2013.01); *B01L 2400/0415* (2013.01)

(58) Field of Classification Search
CPC ....... G01N 11/00; G01N 11/04; B01L 3/5027; B01L 2400/0415
See application file for complete search history.

(56) References Cited

U.S. PATENT DOCUMENTS 5,955,659 A * 9/1999 Gupta ....................... G01F 1/28
340/632
6,938,463 B2 * 9/2005 Ehwald .............. A61B 5/14532
73/53.01
(Continued)

FOREIGN PATENT DOCUMENTS

DE 102006001180 A1 9/2007
EP 1923707 A2 5/2008
(Continued)

OTHER PUBLICATIONS

International Search Report dated Aug. 11, 2016 for PCT/EP2016/060835.
Written Opinion dated Aug. 11, 2016 for PCT/EP2016/060835.

*Primary Examiner* — David A Rogers
(74) *Attorney, Agent, or Firm* — Lucas & Mercanti, LLP

(57) ABSTRACT

Apparatus comprising a micro-rheometer (1) with a micro-channel (2) and a sensor array arranged along the micro-
(Continued)

channel to measure rheological properties of a fluid. The sensor array comprises a plurality of pairs of electrodes (8, 8'), each pair being placed face to face to function as an electronic switch when the fluid flows through them. It further comprises a data acquisition system (10) with an electronic circuit in which each pair of electrodes is connected to an amplifier electronic circuit (11) to ensure an ultra-low electrical current flow through the short-circuit created by the fluid and the pair of electrodes, to avoid damaging the fluid. The invention may be used as a small portable device for medical diagnosis in diseases associated to changes in blood viscosity, operating in a wide range of shear rates.

13 Claims, 16 Drawing Sheets

(56) References Cited

U.S. PATENT DOCUMENTS

| | | | | |
|---|---|---|---|---|
| 7,040,144 B2* | 5/2006 | Spaid | ............... | B01L 3/5027 73/54.05 |
| 7,188,515 B2* | 3/2007 | Burns | ............... | B82Y 15/00 702/50 |
| 7,290,441 B2* | 11/2007 | Baek | ............... | G01N 11/08 73/54.09 |
| 7,454,988 B2* | 11/2008 | Tan | ............... | G01N 1/4055 204/600 |
| 7,909,063 B2* | 3/2011 | Sando | ............... | B01L 3/502715 137/334 |
| 8,056,398 B2* | 11/2011 | Jakli | ............... | G01N 11/16 73/54.41 |
| 9,638,617 B2* | 5/2017 | Birkholz | ............... | G01N 11/16 |
| 9,733,174 B2* | 8/2017 | Morhell | ............... | G01N 11/04 |
| 9,829,389 B2* | 11/2017 | Coursey | ............... | B01L 3/5027 |
| 2003/0041652 A1* | 3/2003 | Spaid | ............... | B01L 3/5027 73/54.05 |
| 2006/0179923 A1* | 8/2006 | Burns | ............... | B82Y 15/00 73/54.07 |
| 2008/0134765 A1 | 6/2008 | Baek | | |
| 2010/0042339 A1 | 2/2010 | Dodge et al. | | |
| 2010/0320088 A1* | 12/2010 | Fouillet | ............... | B01F 3/0807 204/454 |
| 2014/0000344 A1* | 1/2014 | Birkholz | ............... | G01N 11/16 73/31.05 |
| 2016/0207044 A1* | 7/2016 | Collins | ............... | G01N 21/6486 |

FOREIGN PATENT DOCUMENTS

| | | | | | |
|---|---|---|---|---|---|
| FR | 2510257 A1 | 1/1983 | | | |
| GB | 2485965 A | 6/2012 | | | |
| KR | 20130128792 A | * | 11/2013 | ............ | G01N 11/08 |
| WO | WO-2008098714 A1 | * | 8/2008 | ............ | G01N 11/00 |
| WO | 2010040581 A1 | 4/2010 | | | |
| WO | WO-2013005185 A1 | * | 1/2013 | ............ | G01N 11/04 |

* cited by examiner

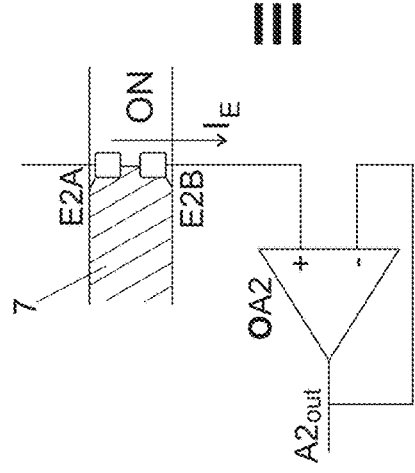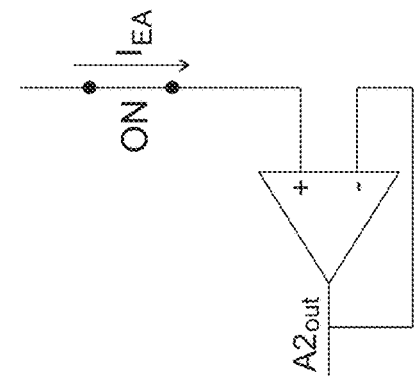
Fig. 5A
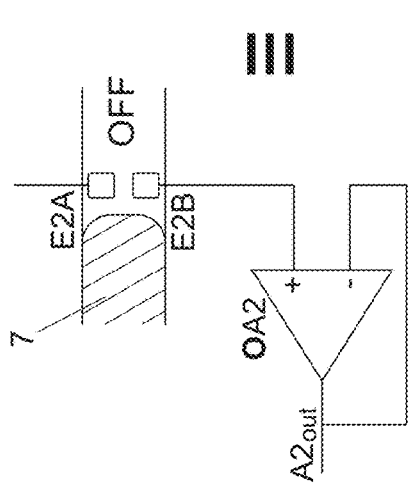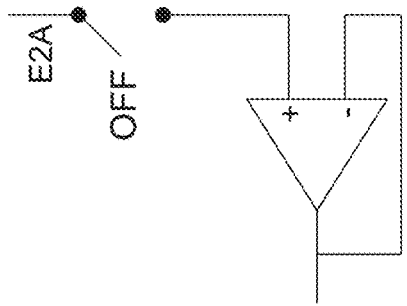
Fig. 5B
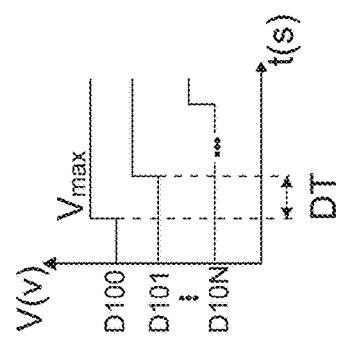
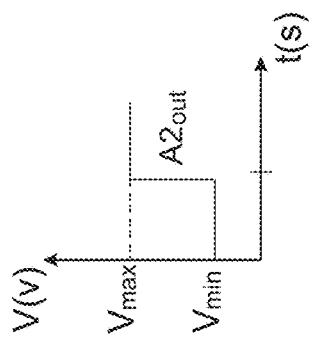

METHOD, APPARATUS AND MICRO-RHEOMETER FOR MEASURING RHEOLOGICAL PROPERTIES OF NEWTONIAN AND NON-NEWTONIAN FLUIDS

CROSS REFERENCE TO RELATED APPLICATION

This Application is a 371 of PCT/EP2016/060835 filed on May 13, 2016, which claims priority of European Application No. 15382248.1 filed May 14, 2015, both of which are incorporated herein by reference.

TECHNICAL FIELD

The present invention concerns to a method and device for measuring the viscosity of Newtonian and non-Newtonian fluids.

BACKGROUND ART

Rheology includes the study of the viscosity in fluid systems and its potential dependence on magnitudes such as the fluid velocity. Usually, macroscopic rheometers are used to measure the viscosity of liquids and suspensions, specifically for those fluids which are characterized by a viscosity which depends upon the values of the velocity of the fluid or the applied pressure.

There is a growing necessity to develop micro-rheometers that take the advantages associated to miniaturized systems: lower volume material, shorter experimental measurements, reduction of costs, and small and portables devices.

Currently, these micro-devices are used as biological or biomedical instruments for sample monitoring (e.g. sugar solutions) and/or medical detection of anomalies (e.g. fluids from knee joints) [Hennemeyer, Marc et al. "Cantilever Micro-rheometer for the characterization of sugar solutions", Sensors 2008. 8, 10-22; Sandia National Laboratories (2012 Sep. 26) "Students painlessly measure knee joint fluids in annual Sandia contest", retrieved from https://share.sandia.gov; Ziemann, F et al. "Local Measurements of Viscoelastic Moduli of entangled actin networks using an oscillating magnetic bead micro-rheometer", biophysical Journal, 1994, Vol. 66, 2210-16]. Furthermore, there are several diseases associated to blood disorders such as leukaemia, cardiovascular disease, sickle cells anaemia, kidney disease, polycythemia, anaemia, etc, that alter the rheological properties of blood, in particular its viscosity.

Several techniques are currently used to develop these micro-biotechnologies, for instance, particle tracking methods where paramagnetic particles are suspended in a viscous fluid. The particles are optically tracked while they are attracted by an external magnetic force. The rheological properties of the fluid are then determined in terms of the behaviour of the tracer particles [previous article of Ziemann, F et al.; Song, Jin-Oh et al. "Magnetic microrheometer for in situ characterization of coating viscosity", Rev. Sci. Instrum., 2010, Vol. 81, 93903 1-8].

More complex micro-electro-mechanical systems (MEMS) are used to study the rheology of fluids. One type of such devices consists of two plates where the fluid sample is placed between them. One plate is fixed while the other plate, controlled by a thermal actuator, moves up and down to deform the sample at different frequencies and measure viscoelastic moduli [Christopher, Gordon F. et al. "Development of a MEMS based dynamic rheometer", Lab Chip, 2010, Vol. 10, 2749-57].

A common feature among most micro-devices for rheological applications is that they are subject to complex analysis, expensive fabrication and/or bulky and expensive equipment to measure the viscosity of fluids.

Moreover, conventional macroscopic rheometers are limited by a minimum torque value that limits the viscosity measurement of fluids of low viscosity values at very low shear rates (or velocities), having as a requirement to perform the measure at higher shears in order to get a valid viscosity result.

Several patent documents refer to rheometers. Patent document US20080134765-A1 discloses a micro-rheometer for measuring flow viscosity and elasticity for micron sample volumes using pressure sensor arrays. The pressure sensors measure the viscosity of the sample liquid while flowing in a uniform length of a flow passage, since from the pressure measurement wall shear stress can be calculated. As it is acknowledged in this patent document, using pressure sensors has several drawbacks, since a perturbation of flow significantly influences pressure measurement, in particular for non-Newtonian liquids. Moreover, any slight surface roughness due to the mounting of pressure sensors may be a source of test sample deposition, which degrades long term performance of the micro-rheometer. There are also some difficulties when mounting individual pressure sensors. Therefore, the measurement accuracy is often compromised depending on how well the individual pressure sensors are mounted in the flow channel. To overcome the problem of patterned structures on flow channel surfaces caused by placement of individual pressure sensors in the flow channel, US20080134765-A1 discloses the use of pressure sensors monolithically integrated into the wall of the flow channel.

However, all these problems are not satisfactorily solved, as explained in patent document GB2485965, which refers to a rheometer for measuring the viscosity and elasticity of liquids. This patent document explains that the previous patent document, US20080134765-A1, embeds the pressure sensors in the body of material defining the flow channel with the aim to ensure that the flow of fluid within the channel is not disturbed by the pressure sensors, in order to obtain a smooth, uninterrupted internal surface of the channel. However, it acknowledges several disadvantages associated with the integrated pressure sensor arrangement:

The apparatus is difficult and expensive to produce.
Once the arrangement has been manufactured there is no flexibility in where to locate the pressure sensors.
The separation of the pressure sensors from the flowing liquid by even a small thickness of material can reduce the accuracy of the pressure measurements obtained from the sample.
It only measures steady state viscosity of sample liquids.

Other patent documents, such as DE102006001180-A1 and FR2510257-A1, employ optical sensors to measure the flow velocity. The disadvantages of these optical approaches rely on integration problems (mismatches) with the coupling of the optical elements and the microscale's fluidic device as well as the use of complex electronic control methods to assure the proper operation and data management of the optical sensors.

Patent document EP1923707-A2 discloses a micro-rheometer with a microchannel and a sensor array arranged to measure rheological properties of a fluid, wherein the sensor array comprises a plurality of pairs of electrodes, the two electrodes of each pair being placed face to face within the microchannel to function as an electronic switch when the fluid flows through them.

Patent document US2010/0042339-A1 discloses a fluidic analysis device for determining characteristics of a fluid, with at least one flow channel, means for directing a fluid into the flow channel, and at least two analytical means suitable for analyzing a sample.

The present invention proposes a different approach to measure the viscosity of Newtonian and non-Newtonian fluids that overcomes some of the above-mentioned problems.

SUMMARY OF INVENTION

The present invention proposes a new method and technique to develop a cheap, easy and portable bio micro-rheometer as a first approach for medical diagnosis in diseases associated to changes in blood viscosity with healthy patients. The device of the present invention is able to operate in a wide range of shear rate, which is proportional to the velocity divided by the gap of the device, controlled by an external pressure source, and has the capacity to analyze any fluid with different viscosity values. The range of pressures used to inject the sample through the device moves from 0.5 KPa up to 250 KPa, although it can handle even higher pressures to work at higher shear rates.

In accordance with one aspect of the present invention, it is provided an apparatus for measuring rheological properties of Newtonian and non-Newtonian fluids, comprising:

At least one micro-rheometer comprising a microchannel with an inlet, an outlet, and a sensor array arranged along the microchannel to measure rheological properties of a fluid flowing through the microchannel; wherein the sensor array comprises a plurality of pairs of electrodes with a known physical disposition along the microchannel, the two electrodes of each pair of electrodes being placed face to face within the microchannel to function as an electronic switch when the fluid flows through them.

A data acquisition system in connection with the sensor array, comprising an electronic circuit connected to the pairs of electrodes and configured for: (i) detecting the timing of the electronic switching, in the electronic circuit, of the pairs of electrodes as the fluid passes by; (ii) obtaining, from the timing of the electronic switching and the physical disposition of the pairs of electrodes, the flow velocity of the fluid inside the microchannel; and (iii) obtaining the rheological properties of the fluid using the acquired flow velocity of the fluid, the dimensions of the micro-rheometer and the pressure at which the fluid is injected in the micro-rheometer; wherein the electronic circuit of the data acquisition system each pair of electrodes is connected to an amplifier electronic circuit to ensure an ultra-low electrical current flow through the short-circuit created by the fluid and the pair of electrodes to avoid damaging the fluid.

In an embodiment, in the apparatus of the present invention the microchannel comprises an inflow section at the inlet and a main channel section where the electrodes are arranged, the cross-section area of the inflow section being smaller than the cross-section area of the main channel section to control the flow velocity of the fluid front inside the main channel.

In other embodiments the apparatus comprises a micro-tube connected to the inlet of the microchannel with a cross-section area smaller than the cross-section area of the microchannel to control the flow velocity of the fluid front inside the main channel.

In other embodiments the apparatus further comprises pneumatic means to inject the fluid inside the micro-rheometer at a determined pressure.

In other embodiments the apparatus comprises an array of micro-rheometers sharing an inlet and with microchannels of different cross-section areas to analyze, at the same time, rheological properties of the fluid at different shear rates.

The electrodes of the micro-rheometer may have an interdigital shape. They may also have a square shape. The electrodes of the micro-rheometer may be placed on the surface of a substrate bound to the microchannel, the substrate being made of PET, glass or any substrate used in microfabrication to deposit, evaporate or print electrode materials.

The micro-rheometer of the apparatus mat be adapted to the analysis of biological samples and be made of biocompatible materials. The micro-rheometer may be adapted to measure the viscosity of the fluid.

Another aspect of the present invention relates to the provision of a micro-rheometer for use in the above-defined apparatus, comprising a microchannel with an inlet, an outlet, and a sensor array arranged along the microchannel to measure rheological properties of a fluid flowing through the microchannel; wherein the sensor array comprises a plurality of pairs of electrodes with a known physical disposition along the microchannel, the two electrodes of each pair of electrodes being placed face to face within the microchannel to function as an electronic switch when the fluid flows through them.

A further aspect of the present invention relates to a method for measuring rheological properties of Newtonian and non-Newtonian fluids. The method comprises:

Injecting at a determined pressure a fluid in the micro-rheometer of the above-defined apparatus.

Detecting the timing of the electronic switching, in the electronic circuit, of the pairs of electrodes as the fluid passes by.

Obtaining, from the timing of the electronic switching and the physical disposition of the pairs of electrodes, the flow velocity of the fluid inside the microchannel.

Obtaining the rheological properties of the fluid using the acquired flow velocity of the fluid, the dimensions of the micro-rheometer and the pressure at which the fluid is injected in the micro-rheometer.

The device has been tested with human blood samples at different blood cell concentration and other non-biological fluids. Besides, the device is extremely accurate, being able to recognize samples with viscosity variations of 0.02 mPa·s between them within an error of 5%.

The use of a simple detection method based on electrodes integrated in the device, allows using any biocompatible materials. The device can be manufactured with rigid substrates such as glass or silicon. Moreover, it can be fabricated using soft biocompatible materials such as PET, resulting in a bending micro-device. This property does not affect in any way the detection system and/or its sensibility.

The method is based on the study of the progression of a fluid front and involves a fluid flow regime. The proposed device allows the control of the front velocity within a microchannel rather than the pressure drop which simplifies the mathematical analysis, resulting in easier and fast data analysis. The micro electro-rheometer of the present invention is cheap, portable, easy to handle and fabricate, and can give the rheological properties of a fluid in less than two minutes. Besides, the device is fabricated with biocompatible materials that can be used in biological and medical applications and at any environmental temperature/conditions.

The micro-device was fabricated and tested using biocompatible materials such as PDMS (Polydimethylsiloxane), PET (Polyethylene Terephthalate) and glass. However, this device can be fabricated with any polymer as longs as it is biocompatible (e.g. PEN (polyethylene naphthalene), PMMA (polymethyl methacrylate), etc.) for the analysis of biological samples. The electrodes used for the detection of the flow front can be made of platinum. However, the fluid detection can be performed with any other conductive material, such as gold, silver, copper, etc. Thus, the micro-rheometer can be fabricated using soft biocompatibles materials, such as PET, resulting in a bending micro-device.

The method allows the measurement of the viscosity of an arbitrary fluid by detecting the velocity of advancement of the fluid front by means of electrodes placed along the length of the microchannel. The key element of the design is the control of the hydrodynamic regime. The main difference with respect to other known methods for measuring the viscosity of the fluid is that these methods are based on direct measurement of the pressure drop at the fluid front. The present method is a much simpler solution, since it only needs to detect the velocity of advancement of the front by means of a device which electrically detects the position and velocity of the front.

The method is based on the detection of the fluid front velocity at different and arbitrary positions along the microchannel, which allows for the arrangement of electrodes to be uniform, thus simplifying the design and fabrication. This method based on the use of electrodes instead of pressure sensors is novel. The use of electrodes simplifies and cheapens the fabrication process in terms of both direct costs and fabrication time.

BRIEF DESCRIPTION OF DRAWINGS

A series of drawings which aid in better understanding the invention and which are expressly related with an embodiment of said invention, presented as a non-limiting example thereof, are very briefly described below.

FIGS. 5A and 5B shows the electrical switch activation by the fluid through the channel.

FIG. 5A shows the switch activation (switch ON) and FIG. 5B shows no detection (switch OFF).

DESCRIPTION OF EMBODIMENTS

Figure 1:
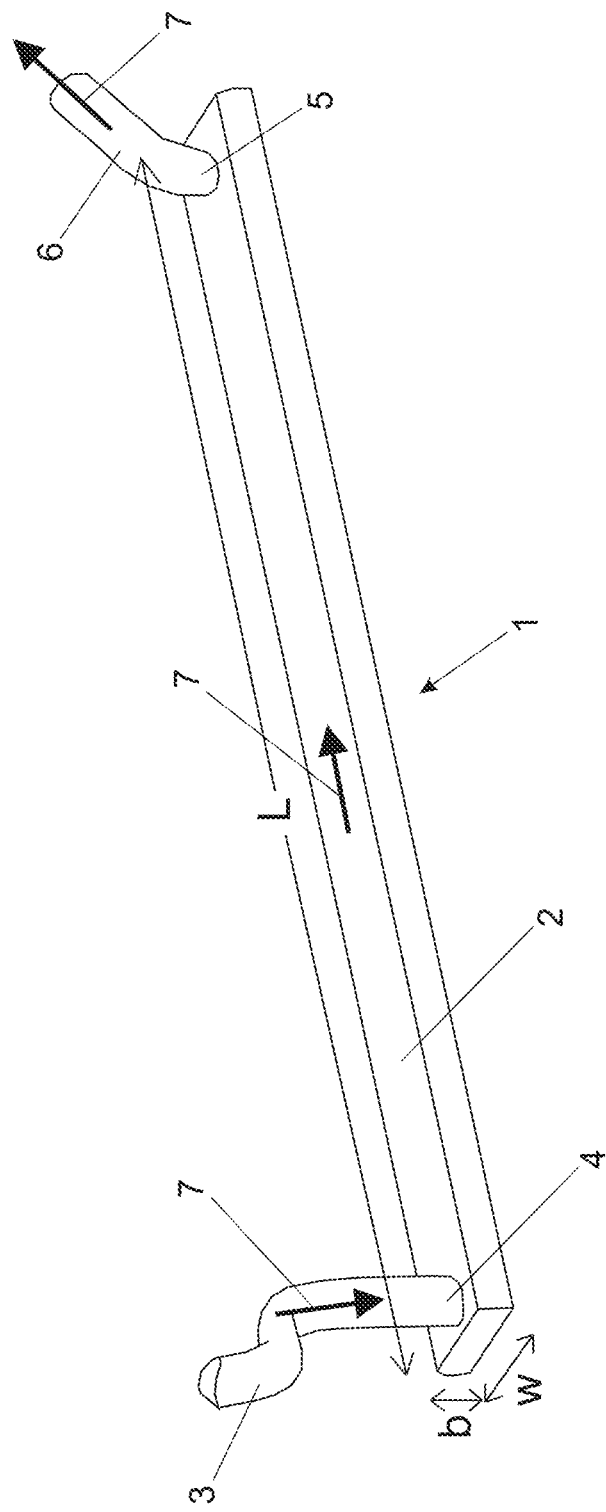
FIG. 1 shows a schematic view of the microchannel of the micro-rheometer according to the present invention.

FIG. 1 shows a schematic view of the microchannel 2 of the micro-rheometer 1 according to the present invention. The test fluid 7 follows an input tube 3 and enters the microchannel 2 through an inlet 4; then, the fluid 7 exits the microchannel 2 through an outlet 5 and output tube 6. The micro-rheometer 1 comprises a straight microchannel 2 with a rectangular shape (length L, width w and height b).

Figure 2:
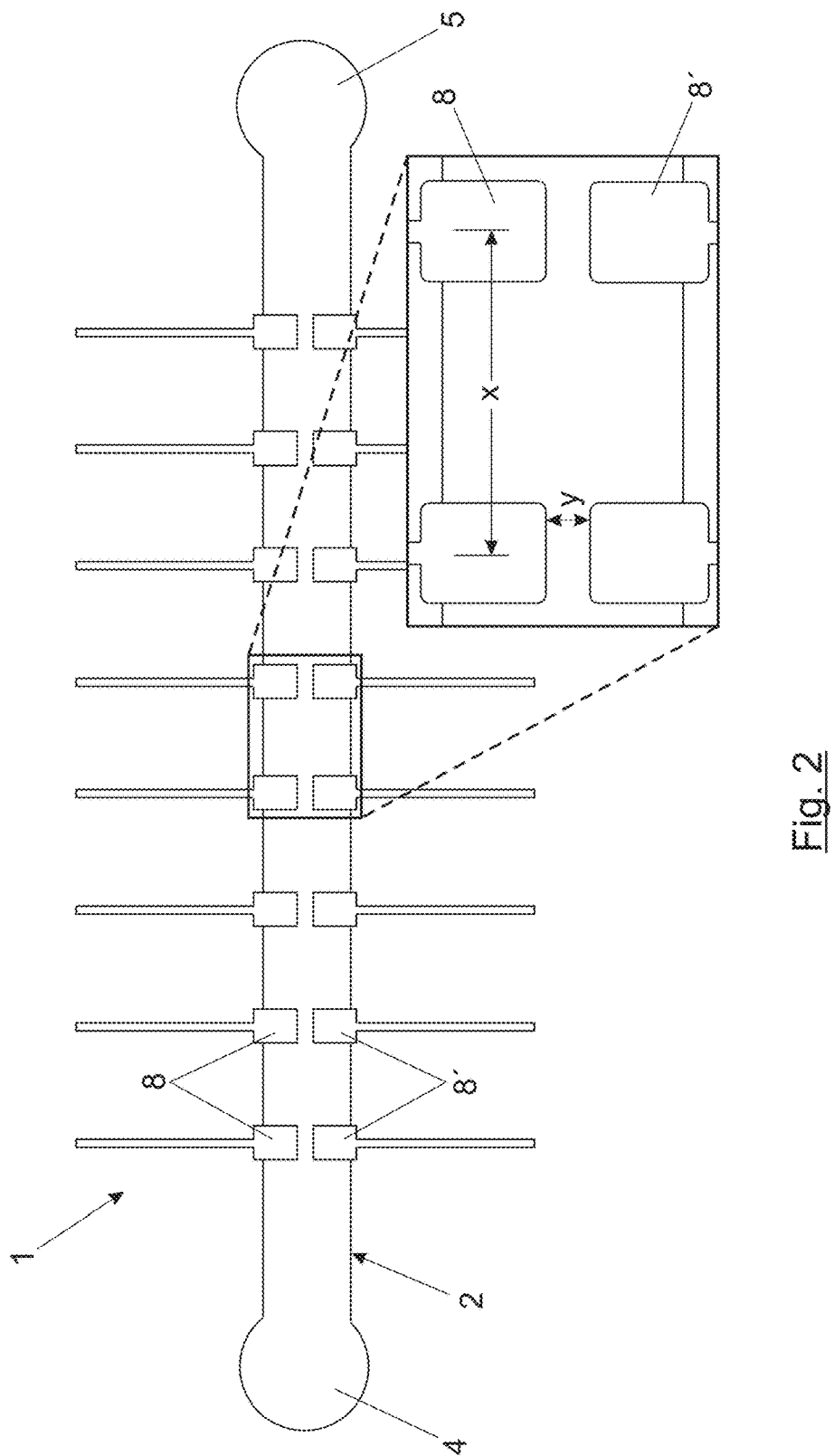
FIG. 2 shows a top view of the electrode array of the micro-rheometer.

The micro-rheometer 1 also comprises an array of pairs of electrodes 8/8' (not shown in FIG. 1) arranged along the microchannel 2, each pair of electrodes being placed face-to-face. FIG. 2 shows a top view of the electrode array of the micro-rheometer 1. The electrodes 8/8' are located equidistant from the central axis of the microchannel 2. In a preferred embodiment the electrodes are made of platinum film deposited on a PET (polyethylene terephthalate) polymer, which is a transparent and biocompatible material commonly used in the food industry. In a preferred embodiment the distance X (shown in a zoom view of FIG. 2) between adjacent pairs of electrodes, measured from center to center, is 1.6 mm, and the distance Y between opposite electrodes of each pair is 250 µm.

Figure 3A:
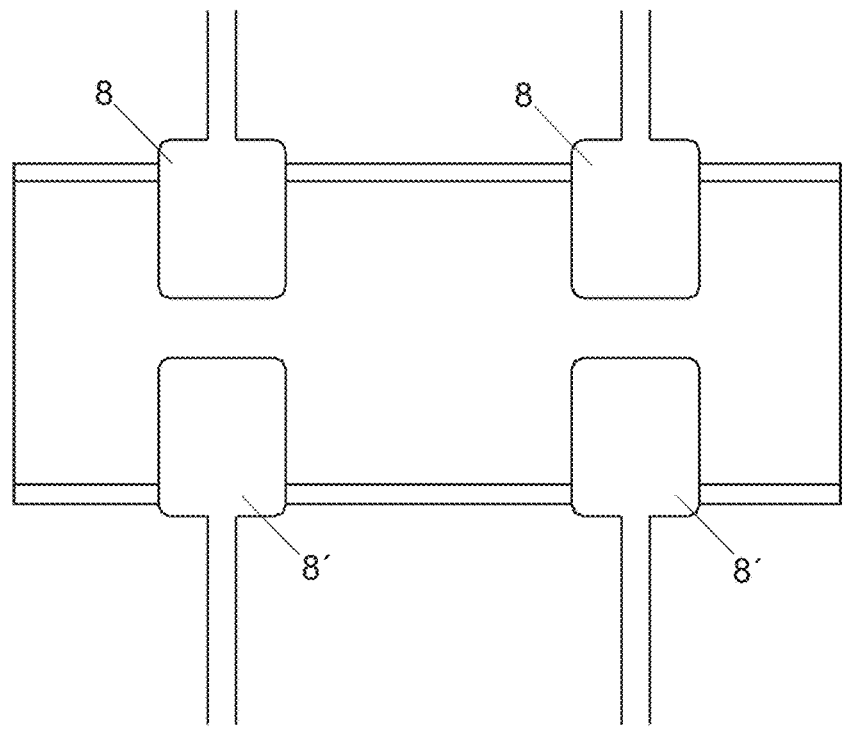
FIGS. 3A and 3B show two different designs of the electrodes.
Figure 3B:
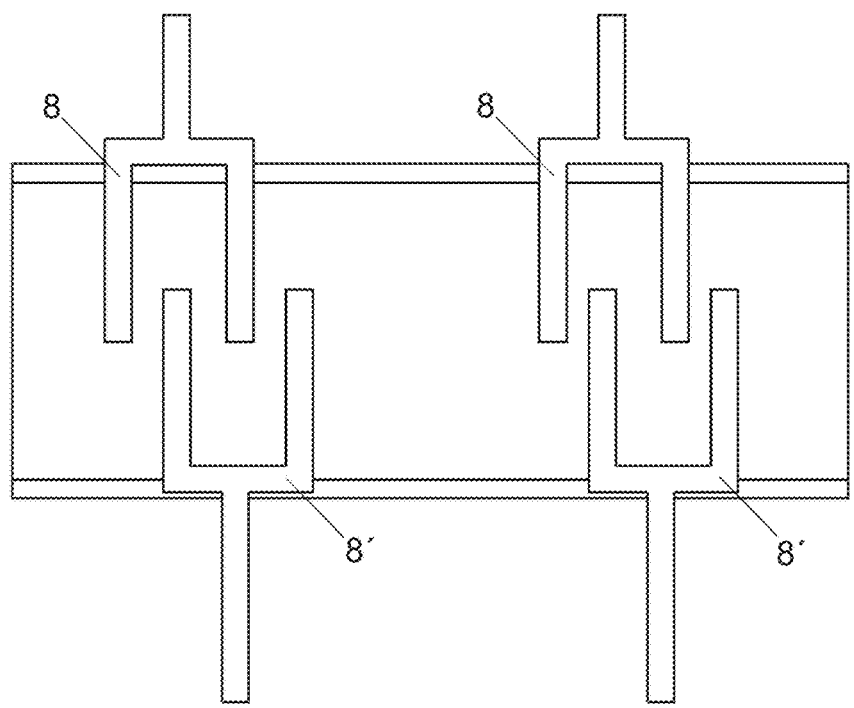

FIGS. 3A and 3B show two different designs of the electrodes used to detect the fluid flow: square (FIG. 3A) and interdigitals (FIG. 3B). Other shapes may also be used.

Figure 4:
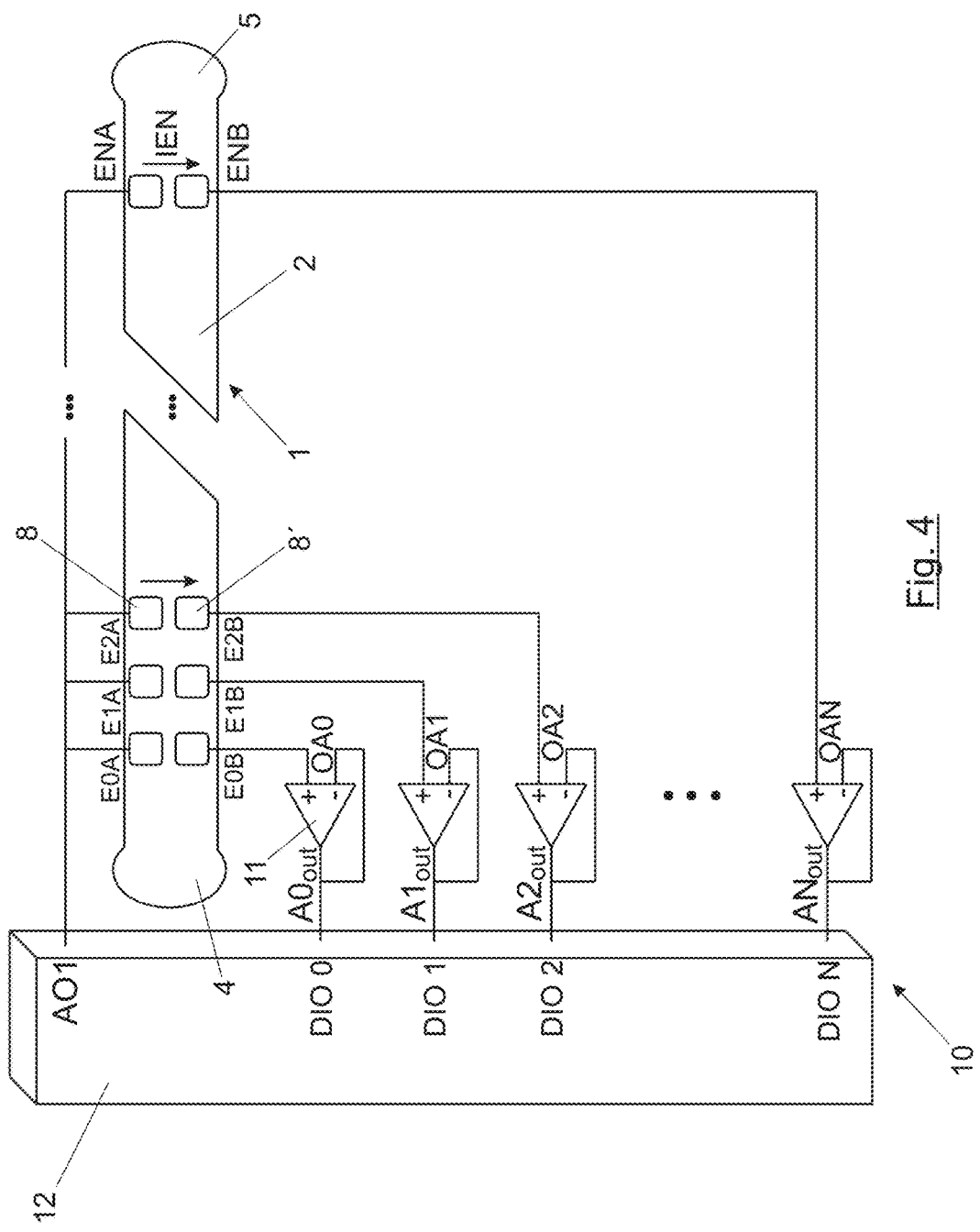
FIG. 4 shows the data acquisition system for the electrical detection of the flow velocity of the fluid within the microchannel.

FIG. 4 shows a data acquisition system 10 used for the electrical detection of the flow velocity of the fluid 7 within the microchannel 2. The data acquisition system 10 may be considered an external element, not forming part of the micro-rheometer 1. In other words, each electrode—E0A, E0B, E1A, E1B, E2A, E2B, . . . ENA, ENB—of the micro-rheometer 1 has an electrical contact to allow connection with the data acquisition system 10. In the example shown in FIG. 4 the electrodes in one side—E0A, E1A, E2A, . . . , ENA—are connected to an analog output AO1 of the data acquisition system 10, whereas the electrodes in the other side—E0B, E1B, E2B, ENB—are each connected to a digital input-output—DIO 0, DIO 1, DIO 2, . . . , DIO N—of the data acquisition system 10.

The detection of the flow velocity is carried out using the electrodes and the electrical circuit depicted in FIG. 4. The circuit is comprised of N pair of electrodes 8/8', N operational amplifiers 11—OA0, OA1, OA2, . . . , OAN—and a data acquisition board 12 with an electronic controller (e.g. microcontroller). The face-to-face electrodes work like two terminals of an electrical switch activated by the fluid 7 through the channel, as shown in FIGS. 5A and 5B. The switch is turned on when the fluid 7 simultaneously reaches the two electrodes, E2A and E2B in FIG. 5A. At that point, a short circuit is created between them and an electrical current circulation starts to flow (FIG. 5A). On the other hand, while the fluid does not contact the electrodes the switch rests at off state (FIG. 5B).

In order to create the electrical current flow, the first terminal E2A of the pair of electrodes 8/8' is connected to a programmable positive potential (analog output AO1) generated by the data acquisition board 12. The second terminal E2B of the pair of electrodes 8/8' is connected to the positive input of the operational amplifier OA2 in a voltage follower configuration. During the off state, the potential (voltage) at electrode E2A is isolated from the electrode E2B and no electrical current is generated. On the other side, during the on state, the voltage at the electrode E2A reaches the electrode E2B through the short circuit originated by the fluidic switch. Thereby, the potential at terminal B is equal to potential at terminal A and is delivered to the corresponding digital input port of the data acquisition board 12 DIO2 by the operational amplifier output voltage $A2_{out}$.

Once the voltage is at the digital input, the control software starts to count the delay time (DT) between the activation of the different electrodes along the channel. The operational amplifier 11 is used to ensure an ultra-low electrical current flow $I_E$ through the short circuit created by the fluid and the terminals to avoid fluid sample damage. This is due to the virtual-ground property and the low-bias current at the input terminals of the operational amplifiers. For the present application, operational amplifiers with a bias current of pico-amperes and femto-amperes are preferably used.

Figure 6:
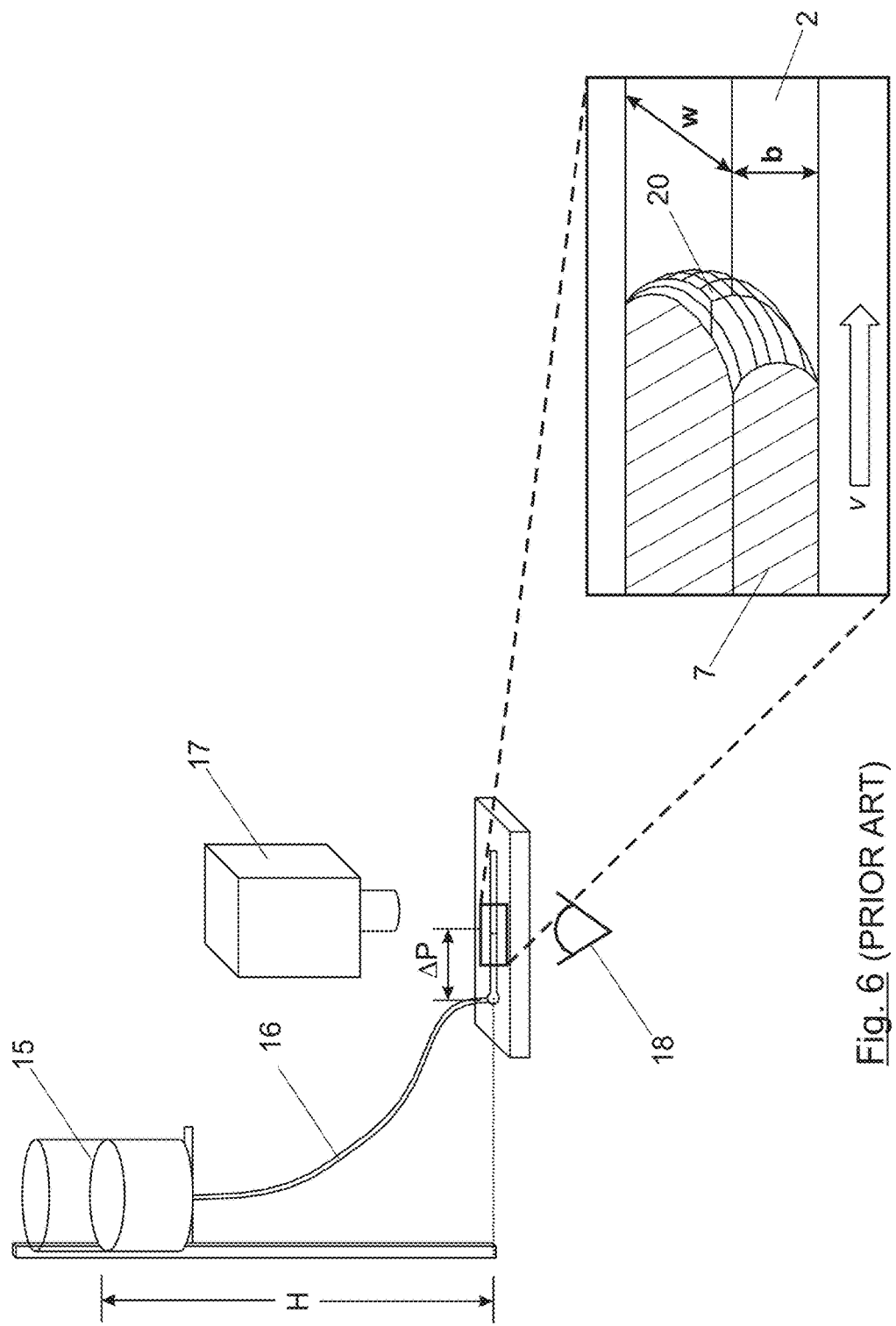
FIG. 6 shows a set up for optical detection, according to the state-of-the-art, of the fluid flow where the liquid is injected using a liquid column.

FIG. 6 shows an example of flow velocity detection using optical means according to the state-of-the-art. In this figure H is the height of the liquid column which determines the global pressure drop, ΔP is the pressure drop between the inlet of the microchannel and the front of the fluid, and v is the velocity of the front. In this example at lower shear rates the pressure drop along the system is controlled using a column of fluid, where the fluid container or reservoir 15 can be set at different heights H to vary the pressure drop, ΔP, resulting in a shear variation. The fluid container 15 is connected to the microchannel by a capillary biocompatible tube 16 of uniform internal circular cross-section of diameter, d. This tube 16 gives control to the flow velocity v, where at high driving pressures the velocity of the fluid mean front 20 inside the microchannel has a rather constant value. Images and videos are acquired using a high speed camera 17 via an inverted microscope 18.

Figure 7:
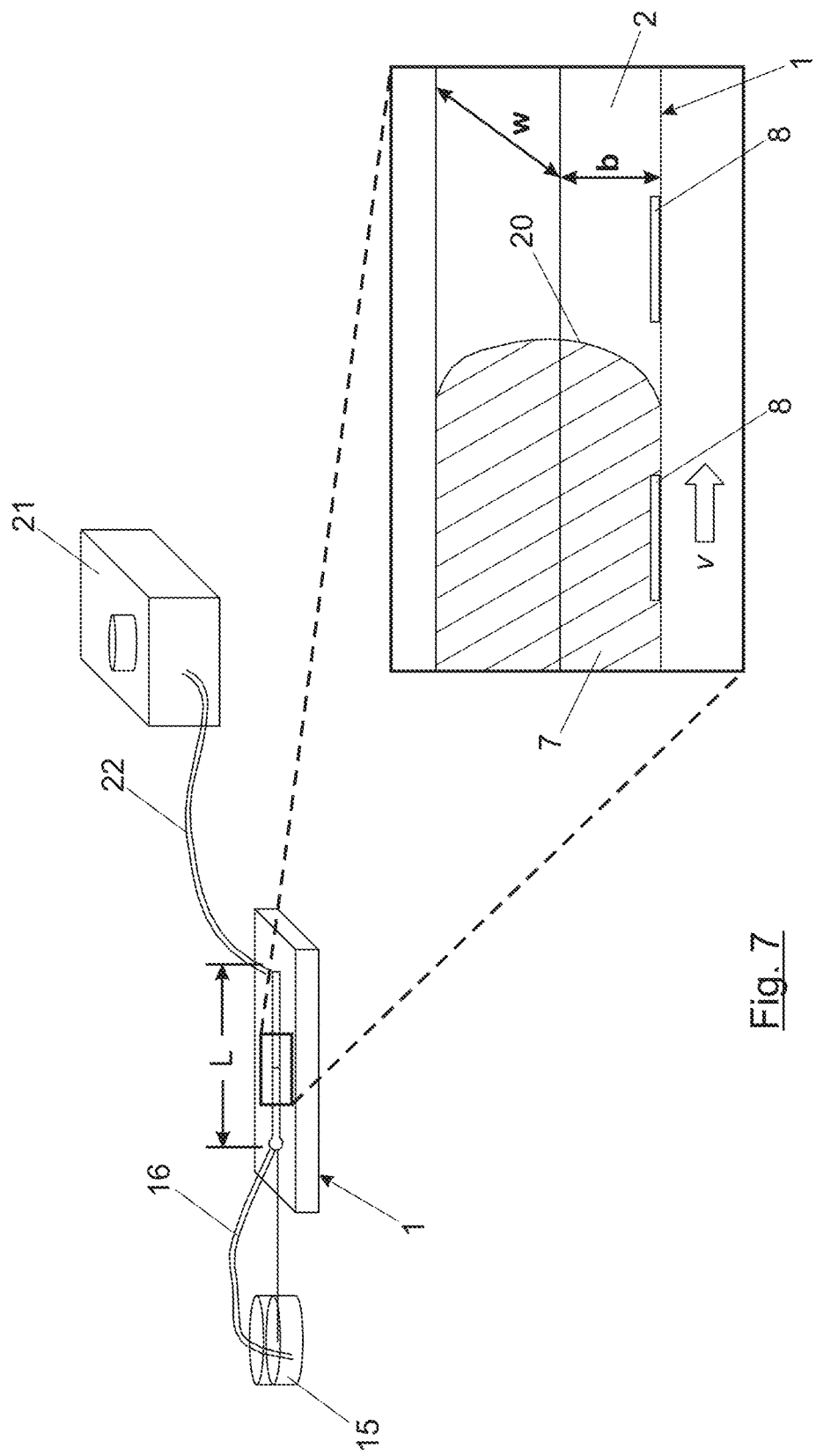
FIG. 7 shows a set up for electrical detection of the fluid flow where the fluid is injected using a suction pump.

FIG. 7 shows a set up for electrical detection, according to the present invention, of the fluid flow where the fluid is injected using a suction pump. High shear rates can be obtained using an external suction pump 21 connected to the micro-rheometer 1 using the capillary tube 22. The flow tracking is performed with the integrated electrodes in the microchannel 2. In different experiments the measures obtained with the micro-rheometer 1 can be corroborated with images obtained with the high speed camera or using a conventional rotational rheometer.

The main aspect for the proper functionality of the whole system is the control of the velocity of the fluid within the microchannel 2 so as to simplify the data analysis. In order to obtain a constant velocity in the channel it is necessary that the inlet of the main channel has a narrower section (with higher flow resistance) as compared with the section of the microchannel 2 (with lower flow resistance). This can be done by using a narrower microchannel connected to the main microchannel 2 (e.g. narrow section 30 with length $l_1$ and gap height b1 connected to the main channel 31 in FIG. 8).

Figure 8:
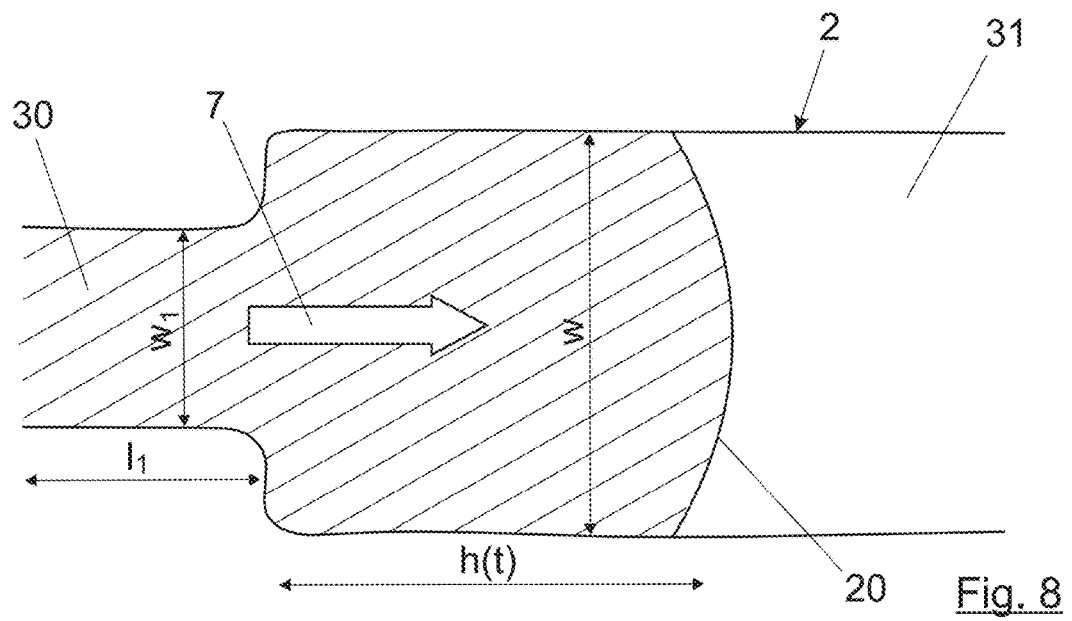
FIG. 8 shows an image of the microchannel structure with a narrower section integrated at the inlet to control the flow velocity.

Regarding the modelling of the system of the example shown in FIGS. 7 and 8, the analysis starts at $t_0$ where the flow front 20 (interface between fluid and air) is placed at the entrance of the microchannel 2. As the fluid flows into the device the fluid front position h(t) increases with time t and the velocity is calculated.

By considering flow conservation within our experimental setup and suitable geometrical conditions which ensure that main contribution to the resistance within the device comes from the narrow section micro-channel (see FIG. 8) which feeds the main micro-channel, a fluid flow regime ensues in which the fluid front velocity is constant. For the fluid front velocity to be constant the geometrical factors of our setup must satisfy:

$$h(t) \ll l_1$$

which implies that the following relation is satisfied:

$$P_{in} - P_{atm} A(n) \gamma^n + P_L \qquad (1)$$

where $P_{in} - P_{atm}$, and $P_L$ are the pressure drop and the capillary pressure, respectively. A(n) is defined as:

$$A(n) = \frac{2^{n+1} l_1}{b} m \left(2 + \frac{1}{n}\right)^n \left(\frac{w}{w_1}\right)^n$$

γ is the shear rate given by:

$$\gamma = 6 \frac{w}{w_1} \frac{h}{b}$$

Finally, the viscosity η is defined as the ratio between the shear stress σ and the shear rate γ:

$$\eta = \frac{\sigma}{\gamma} = m \gamma^{n-1},$$

where the shear stress σ is defined by:

$$\sigma = \frac{b}{2 l_1} (P_{in} - P_{atm} - P_L)$$

The parameters which provide the value of the viscosity as a function of the shear rate, m and n, are obtained by fitting Eq. (1) to experimental data.

Figure 9:
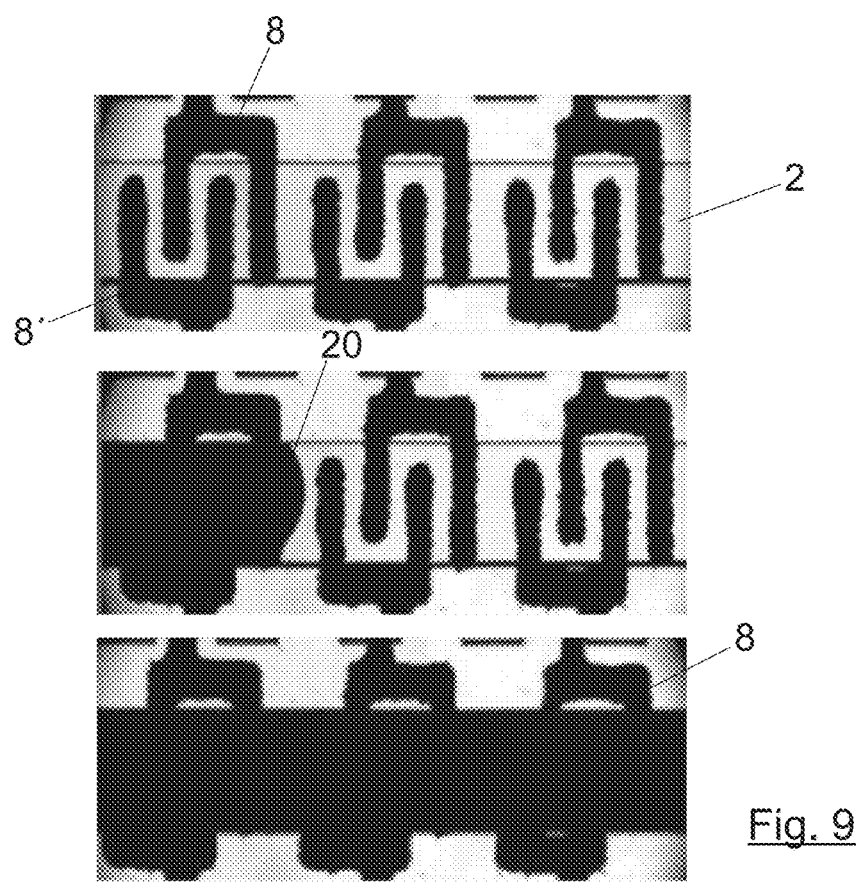
FIG. 9 shows several images, obtained from a data acquisition software, of the electrical detection of the fluid front inside the microchannel as the fluid passes through the electrodes.

The data acquisition system 10 performs a real time monitoring and flow tracking via the electrodes 8/8' integrated or mounted in the microchannel. The electrodes of each pair of electrodes 8/8' located along the microfluidic device, which are facing one another, may have different forms, e.g. square (FIG. 3A) or interdigital (FIG. 3B). As the flow passes through the electrodes, the connectivity between them is activated and a counter is switched on. FIG. 9 represents several images of the electrical detection of the flow velocity performed by the data acquisition software, as the fluid front 20 passes through the pairs of electrodes 8/8'. The counter switches off once the fluid activates the next pair of electrodes. In this way, the time taken by the fluid to flow from one pair of electrodes to the next one can be monitored. Furthermore, as the distance between two electrodes is known, the velocity of the fluid within the microchannel 2 can be computed. This data is recorded and subsequently analyzed to obtain the flow viscosity.

Figure 10:
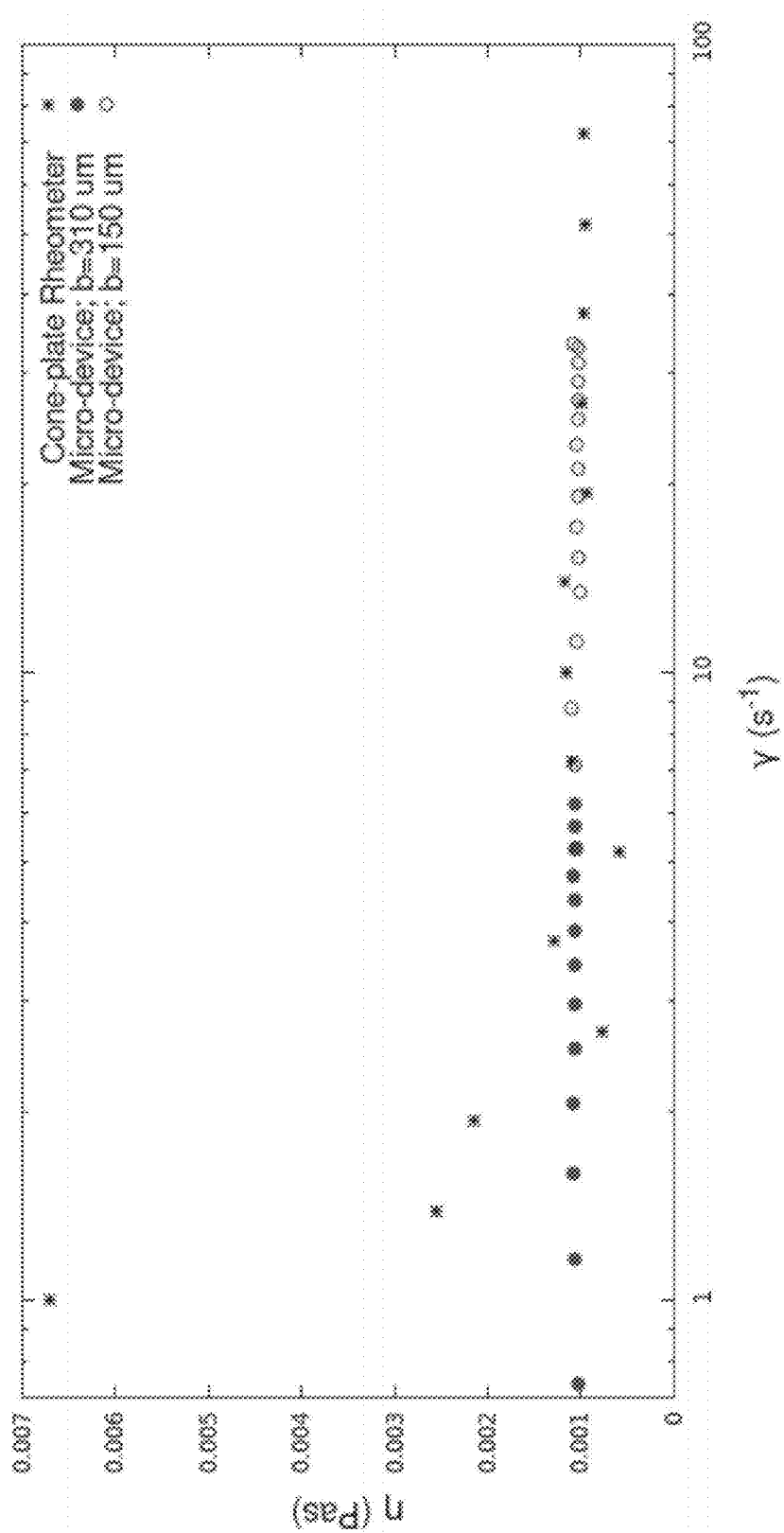
FIG. 10 shows measurements of the viscosity of water measured as a function of the shear rate.

FIG. 10 shows measurements of the viscosity of water n measured as a function of the shear rate $\gamma$. The results obtained with the device of the present invention are compared to those obtained with a commercial rheometer. The present invention measures the viscosity of water accurately in a range of shear rates $\gamma$ beyond the reach of the commercial rheometer. FIG. 10 shows that the measures carried out with a standard bench-top rheometer present high dispersion at shear rates $\gamma$ lower than 6 s$^{-1}$, while the viscosities obtained using the micro-device of the present invention with b=150 µm ($\gamma$=5-12.5 s$^{-1}$) and b=310 µm ($\gamma$=0.01–7 s$^{-1}$) remain constant much before the rheometers stabilizes. Moreover, with the acquired information the shear stress vs. the shear rate $\gamma$ can be determined.

Figure 11A:
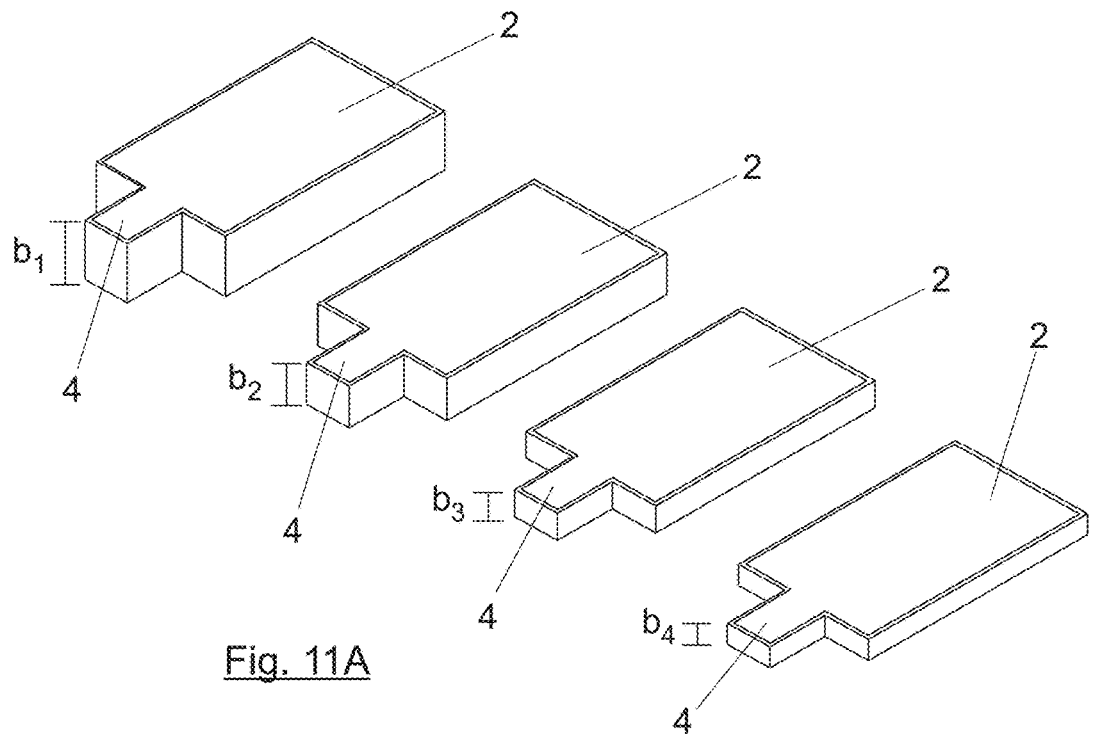
FIG. 11A shows multiple channels with independent inlets between them and different heights.
Figure 11B:
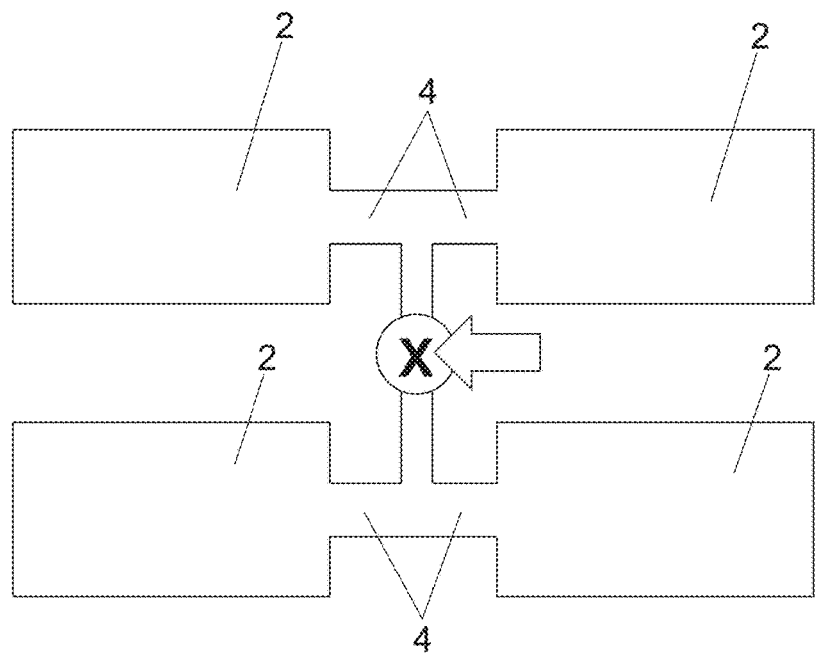
FIG. 11B shows an on-top view of an arrange with multiple micro-channels sharing a unique inlet.

Although we are using two channels with small height (b=150 µm) to achieve higher shear rates and greater height (b=310 µm) to work at lower shear rates, the system can be integrated in an array of multiple microchannels 2 with different heights as shown in FIGS. 11A and 11B.

Figure 12A:
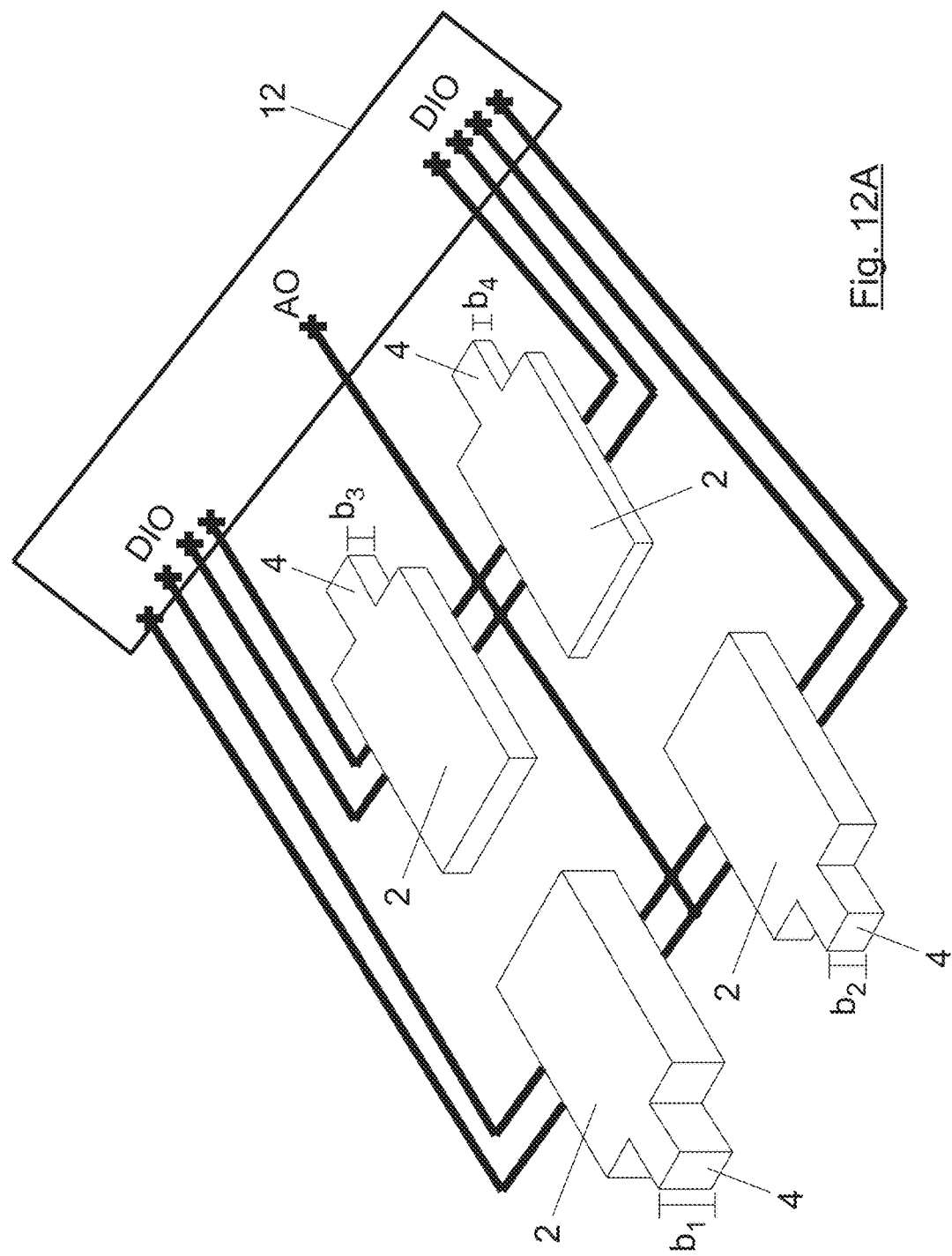
FIG. 12A shows an array of micro-rheometers with independent inlet.
Figure 12B:
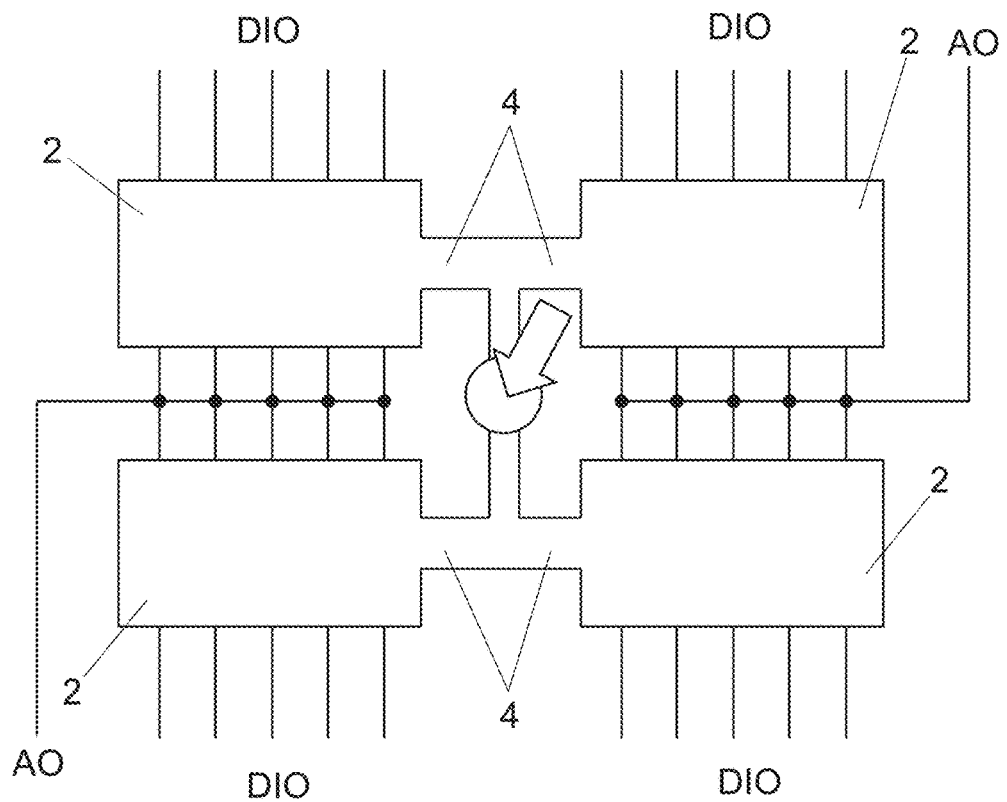
FIG. 12B shows a top view of an array of micro-rheometers sharing the inlet.

Moreover, as in previous microfluidic devices, the electronic system can be integrated to measure different fluids in parallel (an array of micro-rheometers with independent inlets 4 as shown in FIG. 12A) or to analyze the sample at different shear rates (an array of micro-rheometers sharing the inlet 4 as shown in FIG. 12B, having different heights b). The driving electrode 8 is connected to a programmable positive potential (analog output AO) and the sensing electrodes 8' are connected to different digital input-outputs (DIO).

Figure 13:
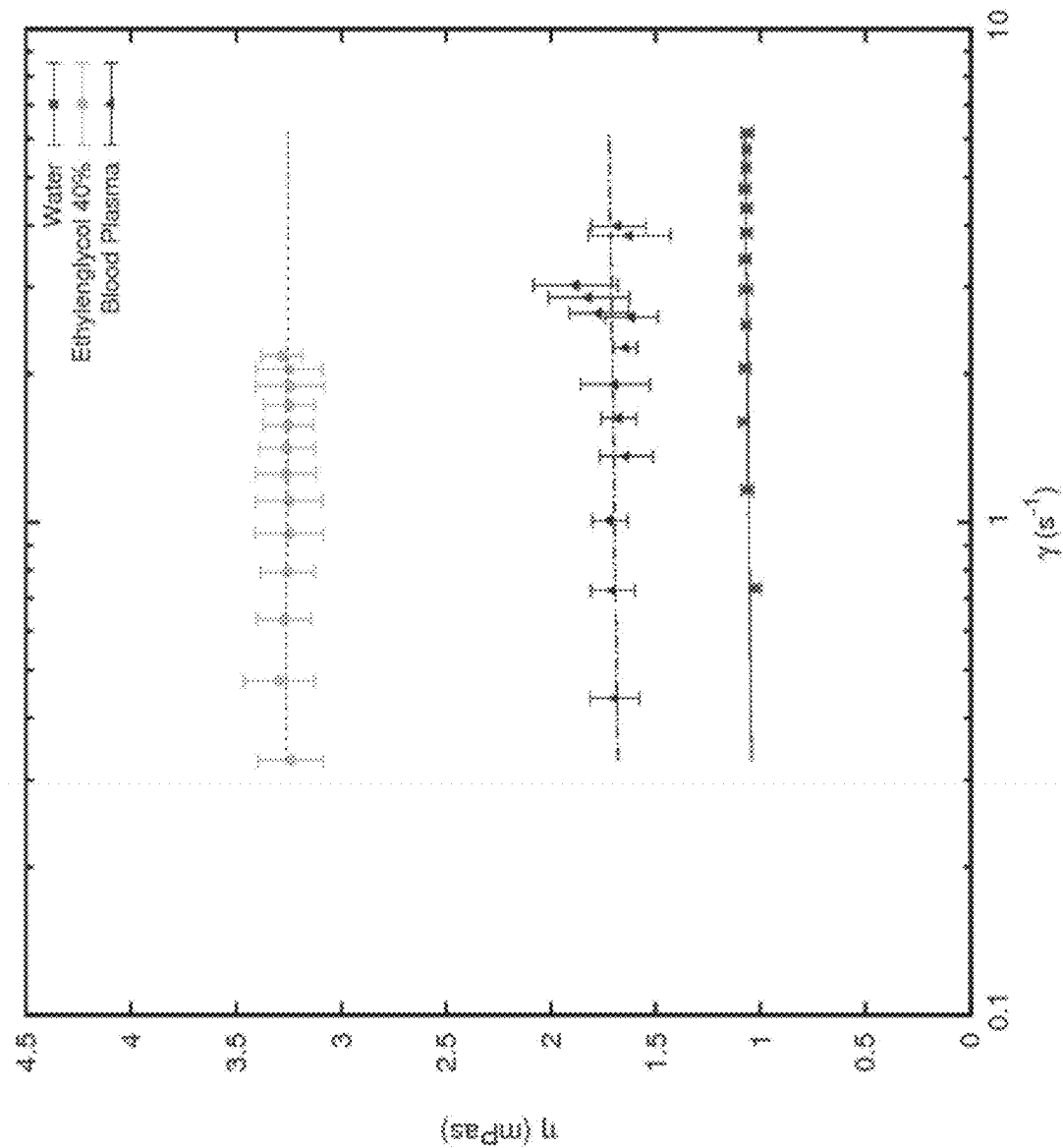
FIG. 13 shows a graph representing viscosity vs shear rate of different fluids (water, ethylene-glycol 40% and blood plasma).

Besides the characterization of the micro-device using a well-known fluid (water), water values are used to study the behavior of biological and non-biological fluids with different viscosities and densities. The viscosity values of water, ethylene-glycol 40% and blood plasma obtained with the micro-rheometer are shown in FIG. 13 (viscosity vs shear rate with height b=310 µm). Moreover, the stress vs shear rate can also be calculated.

Figure 14:
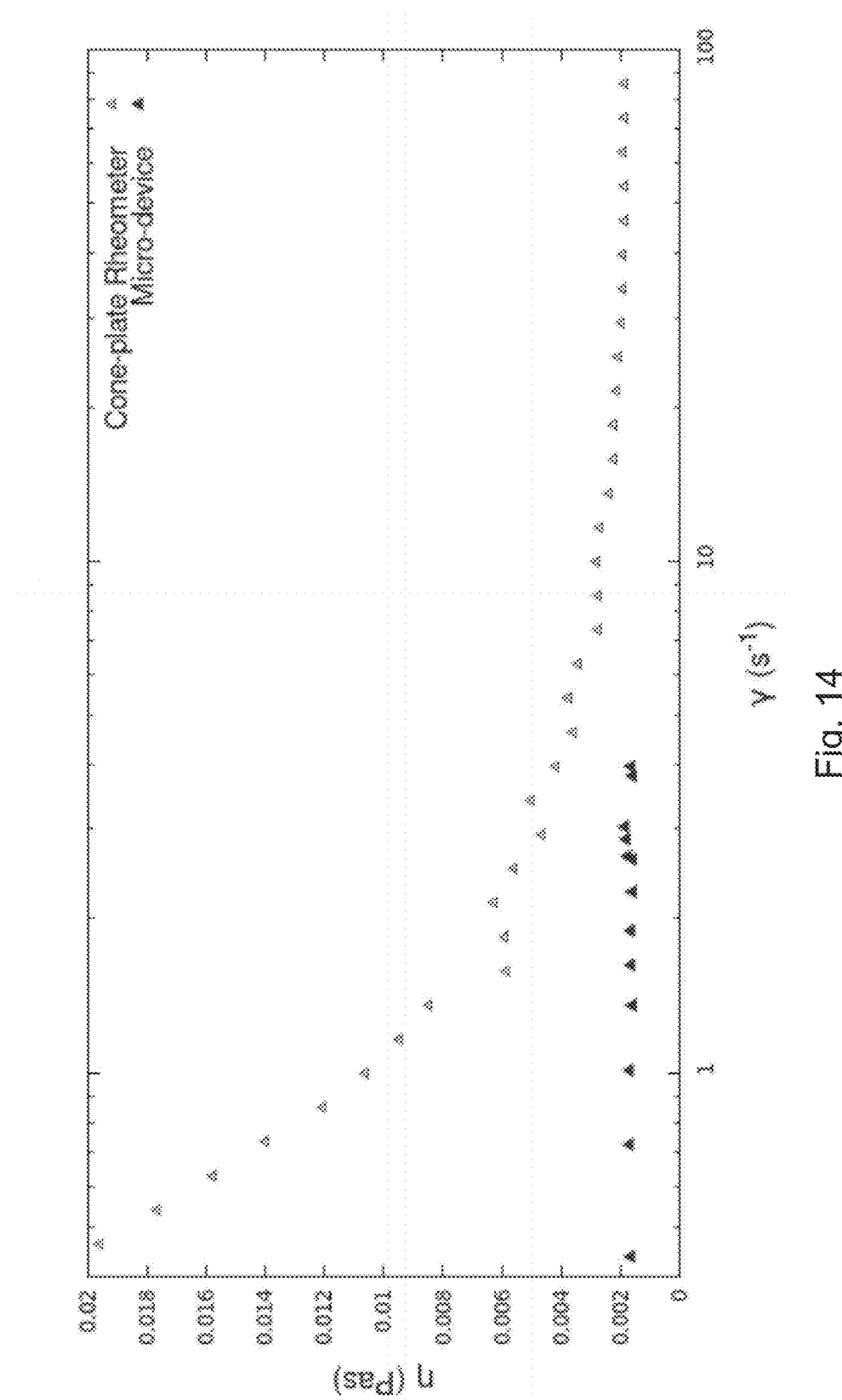
FIG. 14 shows viscosity vs. shear rate measurements for blood plasma obtained from a conventional rheometer and from the micro-rheometer of the present invention.

As it is well known, plasma is 90% water and it has lower viscosity than blood. The blood plasma viscosity was measured with a bench-top rheometer and the micro-device of the present invention to corroborate the results at low shear rate obtained during the characterization of the micro-device. The viscosity values vs shear rate measurements for blood plasma are shown in FIG. 14. The viscosity was measured with the microchannel of height b=310 µm and the values corresponds to the values obtained with conventional rheometers at high shears.

The aim of integrating the electrodes to the microchannel 2 is to develop a micro-rheometer which can obtain the viscosity of fluids without the use of an expensive microscope and high speed camera, and also decreasing time consumption. The whole set up comprises a mechanical base, a microfluidic device with electrodes integrated, data-acquisition software and an electronic controller to avoid damaging in the biological samples connected to a computer. The detection system can be powered via a USB connector. The size of the mechanical microchannel holder can be adapted to be used in the microscope if needed, and the thickness of the whole support allows to be used under a conventional and an inverted microscope.

Figure 15:
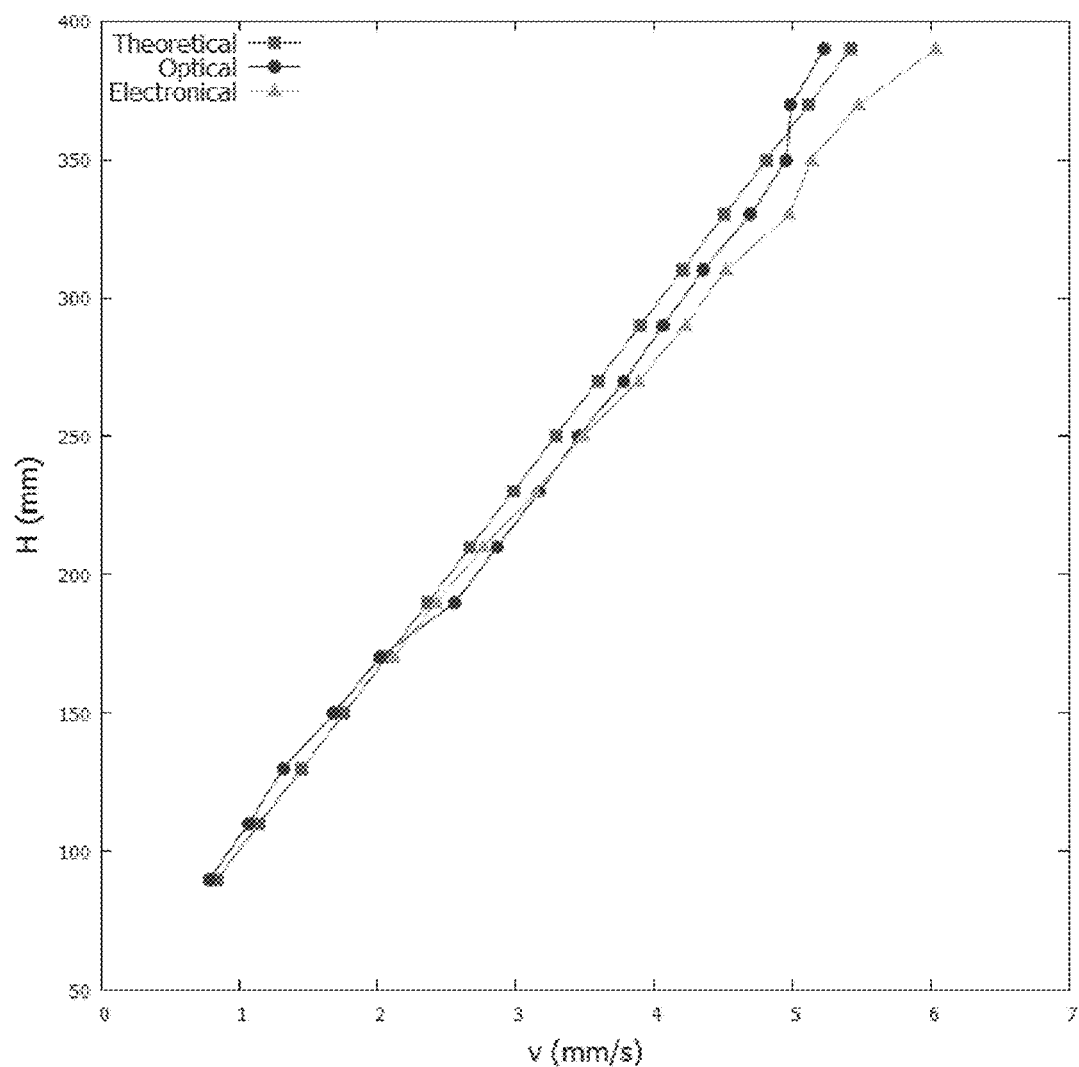
FIG. 15 shows a comparative of fluid velocities obtained with theoretical analysis, with an optical system and with the electronic detection system of the present invention.

The results obtained during the experiments were compared with theoretical values and with values obtained with optical means (FIG. 15 shows height H vs velocity measurements for water and height b=150 µm).

Biomedical devices require a viability test to ensure there is no damage caused to the analyzed samples (e.g. blood samples). These injuries may be caused by chemicals used during the fabrication process, high pressure within the microsystem, electrical detection, samples manipulation, etc. There was no damage caused to the samples manipulated during the experimental studies, resulting in a micro-device able to handle biological samples.

Figure 16:
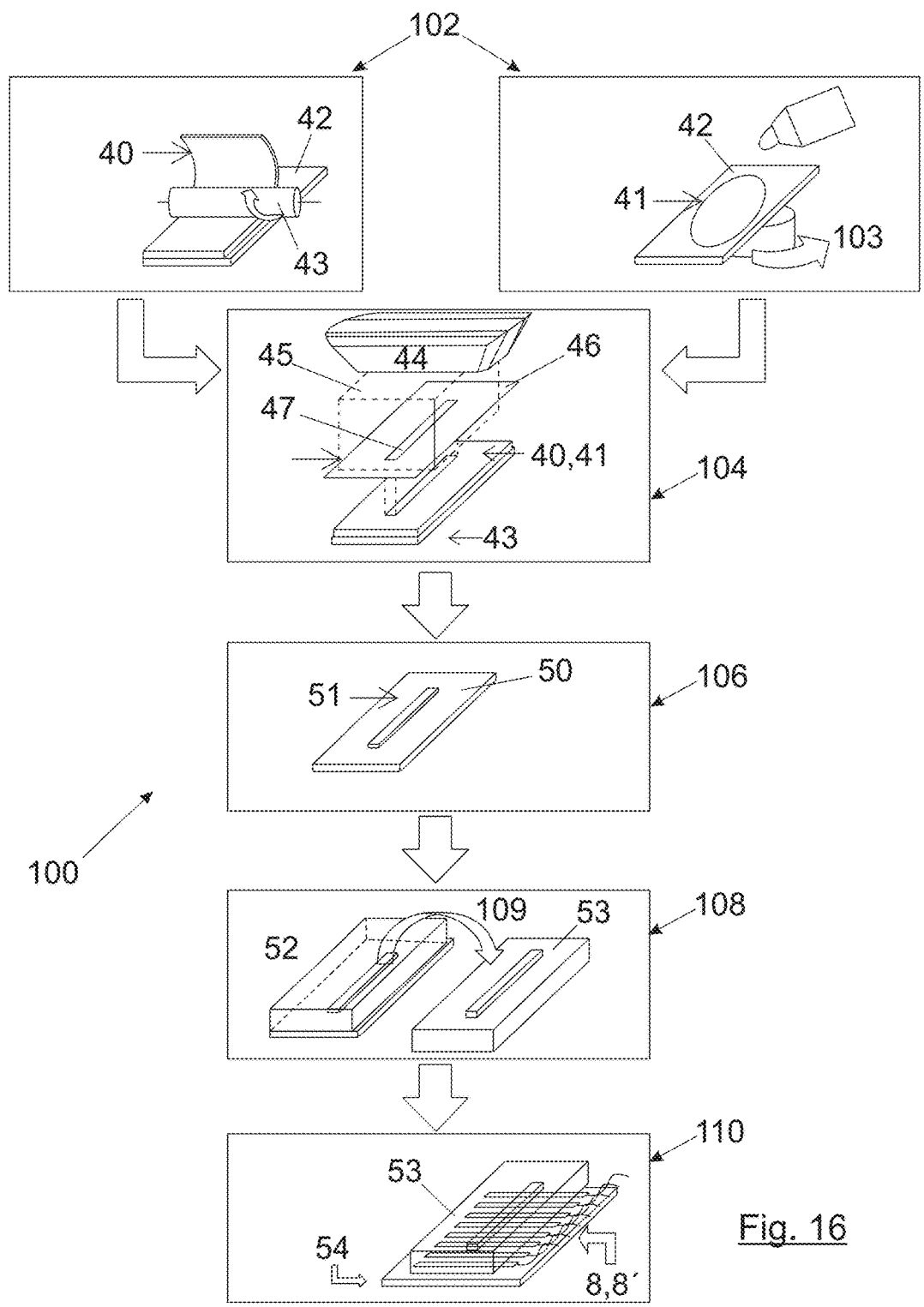
FIG. 16 shows a fabrication process of the micro-rheometer.

FIG. 16 shows a fabrication process 100 of the micro-rheometer 1. During the fabrication process the microchannel moulds can be obtained by different methods, based on soft-lithography technique. Two different photosensitive resist materials can be used: a dry film resist 40 (e.g. Ordyl) or a fluid epoxy-based resist 41 (e.g. SU-8 2150 of Micro-Chem Corp).

A first step of the fabrication process includes thoroughly cleaning the microscope slide with organic solvents (acetone and ethanol) and subsequently, exposing it to plasma cleaning to remove the solvents remaining on the glass surface. Then, the glass substrate is dried with nitrogen and introduced in the oven to dehydrate the surface and increase the adhesion.

The glass substrate 42 is then coated 102 with the photosensitive material 40/41 as follows:

In the first case, the glass surface 42 is spin coated 103 with the fluid epoxy-based resist 41 at 500 rpm for 7 s followed by 3000 rpm (b=200 µm) or 1500 rpm (b=50 µm) during 30 s. Afterwards, it is placed on a hotplate to pre-bake it until solvent content evaporates.

In the same manner, photosensitive dry film resist 40 is placed on the glass substrate 42. In this case a laminator 43 is used to place the film with a controlled temperature.

Once the glass substrate 42 has been covered with the phoresensitive material 40/41, it is exposed 104 to UV light 45 from a UV lamp 44 through a mask 46, which contains the channel geometry 47, for a few seconds and place it on the hotplate to post bake the substrate. Afterwards, the substrate is soaked in a developer solution to obtain 106 the microchannel mould 50 with the microchannel structure 51.

The structure in then replicated 108 using a biocompatible, transparent and hydrophobic material (e.g. Polydymetilsiloxane-PDMS from Sylgard), obtaining a replica mould 52. The PDMS polymer is a result of mixing silicone base and curing agent in a 10:1 ratio by weight. The mixture is degassed under vacuum to remove air bubbles, poured onto the microchannel mold and remains at room temperature until cured.

Afterwards, the PDMS polymer is peeled off 109 from the mould 52. Through-holes are punched in each side of the PDMS channel 53 to get the inlet and outlet of the device and finally are sealed 110 with a clean glass substrate or with PET 54 where the electrodes 8/8' have been deposited.

Bounding the channel 53 with the glass substrate 54 consists in exposing both surfaces to an oxygen plasma treatment for 9 s to create hydroxyl group and get a covalent bonding between them. On the other hand, when bonding PET and PDMS, first they are subjected to an oxygen plasma testament for 1 min and submerge them into an aqueous silane solution. PET is placed into a container with 99% water and 1% of GPTES 98% (3-Glycidoxypropyl triethoxysilane); similarly, glass is placed into an aqueous solution of 99% water and 1% of APTES 99% (3-Aminopropyl triethoxysilane). After 20 min they are thoroughly washed, dried with nitrogen and placed together for an hour at room temperature.

The invention claimed is:

1. An apparatus for measuring rheological properties of Newtonian and non-Newtonian fluids, comprising:

at least one micro-rheometer comprising a microchannel with an inlet, an outlet, and a sensor array arranged along the microchannel to measure rheological properties of a fluid flowing through the microchannel; wherein the sensor array comprises a plurality of pairs of electrodes with a known physical disposition along the microchannel, the two electrodes of each pair of electrodes being placed face to face within the microchannel to function as an electronic switch when the fluid flows through them; and a data acquisition system in connection with the sensor array, comprising an electronic circuit connected to the pairs of electrodes and configured for:

detecting the timing of the electronic switching, in the electronic circuit, of the pairs of electrodes as the fluid passes by, obtaining, from the timing of the electronic switching and the physical disposition of the pairs of electrodes, the flow velocity of the fluid inside the microchannel, and obtaining the rheological properties of the fluid using the acquired flow velocity of the fluid, the dimensions of the micro-rheometer and the pressure at which the fluid is injected in the micro-rheometer;

wherein in the electronic circuit of the data acquisition system each pair of electrodes is connected to an amplifier electronic circuit to ensure an ultra-low electrical current flow ($I_E$) through the short-circuit created by the fluid and the pair of electrodes to avoid damaging the fluid.

2. The apparatus according to claim 1, wherein the microchannel comprises an inflow section at the inlet and a main channel section where the electrodes are arranged, the cross-section area of the inflow section being smaller than the cross-section area of the main channel section to control the flow velocity of the fluid front inside the main channel.

3. The apparatus according to claim 1, further comprising a micro-tube connected to the inlet of the microchannel with a cross-section area smaller than the cross-section area of the microchannel to control the flow velocity of the fluid front inside the main channel.

4. The apparatus according to claim 1, further comprising pneumatic means to inject the fluid inside the micro-rheometer at a determined pressure.

5. The apparatus according to claim 1, comprising an array of micro-rheometers sharing an inlet and with microchannels of different cross-section areas to analyze, at the same time, rheological properties of the fluid at different shear rates.

6. The apparatus according to claim 1, wherein the electrodes of the micro-rheometer have an interdigital shape.

7. The apparatus according to claim 1, wherein the electrodes of the micro-rheometer have a square shape.

8. The apparatus according to claim 1, wherein the electrodes of the micro-rheometer are placed on the surface of a substrate bound to the microchannel.

9. The apparatus according to claim 8, wherein the substrate is made of PET, glass or any substrate used in microfabrication to deposit, evaporate or print electrode materials.

10. The apparatus according to claim 1, wherein the micro-rheometer is adapted to the analysis of biological samples and is made of biocompatible materials.

11. The apparatus according to claim 1, wherein the micro-rheometer is adapted to measure the viscosity of the fluid.

12. A micro-rheometer comprising the apparatus according to claim 1.

13. A method for measuring rheological properties of Newtonian and non-Newtonian fluids, comprising:

injecting at a determined pressure a fluid in the micro-rheometer of an apparatus as defined in claim 1;

detecting the timing of the electronic switching, in the electronic circuit, of the pairs of electrodes as the fluid passes by;

obtaining, from the timing of the electronic switching and the physical disposition of the pairs of electrodes, the flow velocity of the fluid inside the microchannel; and obtaining the rheological properties of the fluid using the acquired flow velocity of the fluid, the dimensions of the micro-rheometer and the pressure at which the fluid is injected in the micro-rheometer.

* * * * *